(12) United States Patent
Hwang et al.

(10) Patent No.: US 11,660,072 B2
(45) Date of Patent: May 30, 2023

(54) PROBE AND SYSTEM FOR IMAGING DENTAL STRUCTURE COMPRISING THE SAME

(71) Applicants: Daegu Gyeongbuk Institute of Science and Technology, Daegu (KR); SNU R & DB FOUNDATION, Seoul (KR); The Industry & Academic Cooperation in Chungnam National University (IAC), Daejeon (KR)

(72) Inventors: Jae Youn Hwang, Daegu (KR); Ji Hun Kim, Changwon-si (KR); Teo Jeon Shin, Seoul (KR); Hong-Keun Hyun, Seoul (KR); Hyoun Joong Kong, Seoul (KR)

(73) Assignees: Daegu Gyeongbuk Institute of Science and Technology, Daegu (KR); SNU R&DB FOUNDATION, Seoul (KR); The Industry & Academic Cooperation in Chungnam National University (IAC), Daejeon (KR)

( * ) Notice: Subject to any disclaimer, the term of this patent is extended or adjusted under 35 U.S.C. 154(b) by 208 days.

(21) Appl. No.: 16/839,444

(22) Filed: Apr. 3, 2020

(65) Prior Publication Data
US 2020/0315578 A1 Oct. 8, 2020

(30) Foreign Application Priority Data
Apr. 4, 2019 (KR) .................. 10-2019-0039574

(51) Int. Cl.
*A61B 8/00* (2006.01)
*G06T 7/00* (2017.01)

(52) U.S. Cl.
CPC .......... *A61B 8/4444* (2013.01); *A61B 8/4483* (2013.01); *A61B 8/56* (2013.01); *G06T 7/0012* (2013.01); *G06T 2207/10024* (2013.01); *G06T 2207/10028* (2013.01); *G06T 2207/10132* (2013.01); *G06T 2207/30036* (2013.01)

(58) Field of Classification Search
CPC ....... A61B 8/4444; A61B 8/4483; A61B 8/56; G06T 7/0012; G06T 2207/10024; G06T 2207/10028; G06T 2207/10132; G06T 2207/30036
See application file for complete search history.

(56) References Cited

U.S. PATENT DOCUMENTS 6,405,071 B1 6/2002 Analoui
10,105,062 B2 * 10/2018 Wang .................. A61B 5/0068
(Continued)

FOREIGN PATENT DOCUMENTS

JP 2003153848 * 12/2004
JP 2013252428 A 12/2013
(Continued)

*Primary Examiner* — Vu Le
*Assistant Examiner* — Winta Gebreslassie
(74) *Attorney, Agent, or Firm* — von Briesen & Roper, s.c.

(57) ABSTRACT

A probe includes a working channel, at least one optical element provided in the working channel and configured to acquire a spectral image of surface information of an object, and an ultrasonic transducer arranged in the working channel and configured to acquire an ultrasonic image of depth information of the target and move with respect to the at least one optical element.

10 Claims, 7 Drawing Sheets

(56) References Cited

U.S. PATENT DOCUMENTS

| | | | |
|---|---|---|---|
| 2014/0193053 A1 | 7/2014 | Kadoury et al. | |
| 2015/0216398 A1* | 8/2015 | Yang | G02B 23/26 600/109 |
| 2018/0296098 A1* | 10/2018 | Islam | G01N 21/35 |
| 2020/0155285 A1* | 5/2020 | Pesach | A61C 9/008 |
| 2020/0352447 A1* | 11/2020 | Tokita | A61B 8/4416 |

FOREIGN PATENT DOCUMENTS

| | | | |
|---|---|---|---|
| KR | 2016-0041803 A | | 4/2016 |
| KR | 2017-0086276 | | 7/2017 |
| KR | 20180077966 A | * | 7/2018 |
| KR | 20180077966 A | | 7/2018 |

* cited by examiner

PROBE AND SYSTEM FOR IMAGING DENTAL STRUCTURE COMPRISING THE SAME

CROSS-REFERENCE TO RELATED APPLICATION(S)

This application claims the benefit of Korean Patent Application No. 10-2019-0039574, filed on Apr. 4, 2019, in the Korean Intellectual Property Office, the disclosure of which is incorporated herein by reference.

BACKGROUND

1. Field of the Invention

One or more example embodiments relate to a probe and a dental structure imaging system including the same.

2. Description of the Related Art

Technology for three-dimensionally modeling a dental structure such as a root canal and accurately measuring the length of the root canal is being developed. For example, there is a direct digital radiology (DDR) technique using an electronic sensor to acquire a radiographic image of a root canal. However, this technique requires imaging equipment of a considerable size, for which a patient may dislike using the equipment, acquires three-dimensional (3D) images of quite low quality since the position of the imaging equipment needs to be changed, and still has an issue of radiation exposure due to the use of radiation.

PRIOR ART DOCUMENT

[Patent Document]
(Patent Document 1) US Patent Publication No. 6,405,071 (published on Jan. 1, 2011)

SUMMARY

An aspect provides a probe and a dental structure imaging system including the same that may acquire an image of a structure of an object using both an optical signal and an ultrasonic signal.

Another aspect also provides a probe and a dental structure imaging system including the same that may use equipment with a smaller size to prevent a patient's dislike and improve spatial accessibility.

Still another aspect also provides a probe and a dental structure imaging system including the same that may obtain both surface information and depth information of a structure in the same field of view.

According to an aspect, there is provided a probe including a working channel, at least to one optical element provided in the working channel and configured to acquire a spectral image of surface information of an object, and an ultrasonic transducer arranged in the working channel and configured to acquire an ultrasonic image of depth information of the target and move with respect to the at least one optical element.

The at least one optical element may be positioned at the center of the working channel, and the ultrasonic transducer may be positioned on an outer side of the at least one optical element.

The ultrasonic transducer may be configured to rotate about the at least one optical element.

The working channel may further include an arcuate slot extending along at least a portion in the vicinity of the at least one optical element, such that the ultrasonic transducer moves therein.

The working channel may further include a limiter provided along a remaining portion in the vicinity of the at least one optical element and configured to limit a movement of the ultrasonic transducer.

The probe may further include a driver configured to generate power, and a drive shaft configured to adjust a direction of a beam of the ultrasonic transducer by receiving the power from the driver and adjusting a rotation of the ultrasonic transducer and an angle with respect to an axial direction.

The working channel may have a shape curved in a length direction thereof, and the drive shaft may extend along the curved shape.

According to an aspect, there is provided a system for imaging a dental structure including a probe configured to be positioned in a dental structure, a spectral image acquisition module configured to acquire a spectral image of surface information of the dental structure, an ultrasonic image acquisition module configured to acquire an ultrasonic image of depth information of the dental structure, and a processor configured to register the spectral image and the ultrasonic image.

The system may further include a color image acquisition module configured to acquire a color image of the dental structure, wherein the processor may be configured to register the spectral image and the ultrasonic image to the color image.

The probe may further include a lens configured to collect an optical signal from the dental structure, and at least one optical fiber configured to transmit the optical signal collected by the lens, wherein the spectral image acquisition module may include a filter wheel including a plurality of filters configured to receive the optical signal by selecting a wavelength of the optical signal received from the optical fiber.

The probe may further include an ultrasonic transducer configured to transmit and receive an ultrasonic signal, and the ultrasonic image acquisition module may include a pulser configured to adjust a pulse of the ultrasonic signal, a receiver configured to receive the ultrasonic signal, and a switch configured to open and close a signal transmission between the ultrasonic transducer and the receiver.

Additional aspects of example embodiments will be set forth in part in the description which follows and, in part, will be apparent from the description, or may be learned by practice of the disclosure.
Effects According to example embodiments, a probe and a dental structure imaging system including the same may use equipment with a smaller size to prevent a patient's dislike and improve spatial accessibility.

According to example embodiments, a probe and a dental structure imaging system to including the same may obtain both surface information and depth information of a structure in the same field of view.

The effects of the probe and the dental structure imaging system including the same are not limited to the above-mentioned effects. And, other unmentioned effects can be clearly understood from the above description by those having ordinary skill in the technical field to which the present disclosure pertains.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Hereinafter, example embodiments will be described in detail with reference to the illustrative drawings. Regarding the reference numerals assigned to the components in the drawings, it should be noted that the same components will be designated by the same reference numerals, wherever possible, even though they are shown in different drawings. Further, in the following description of the present example embodiments, a detailed description of publicly known configurations or functions incorporated herein will be omitted when it is determined that the detailed description obscures the subject matters of the present example embodiments.

In addition, the terms first, second, A, B, (a), and (b) may be used to describe constituent elements of the example embodiments. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The constituent element, which has the same common function as the constituent element included in any one example embodiment, will be described by using the same name in other example embodiments. Unless disclosed to the contrary, the configuration disclosed in any one example embodiment may be applied to other example embodiments, and the specific description of the repeated configuration will be omitted.

Figure 1:
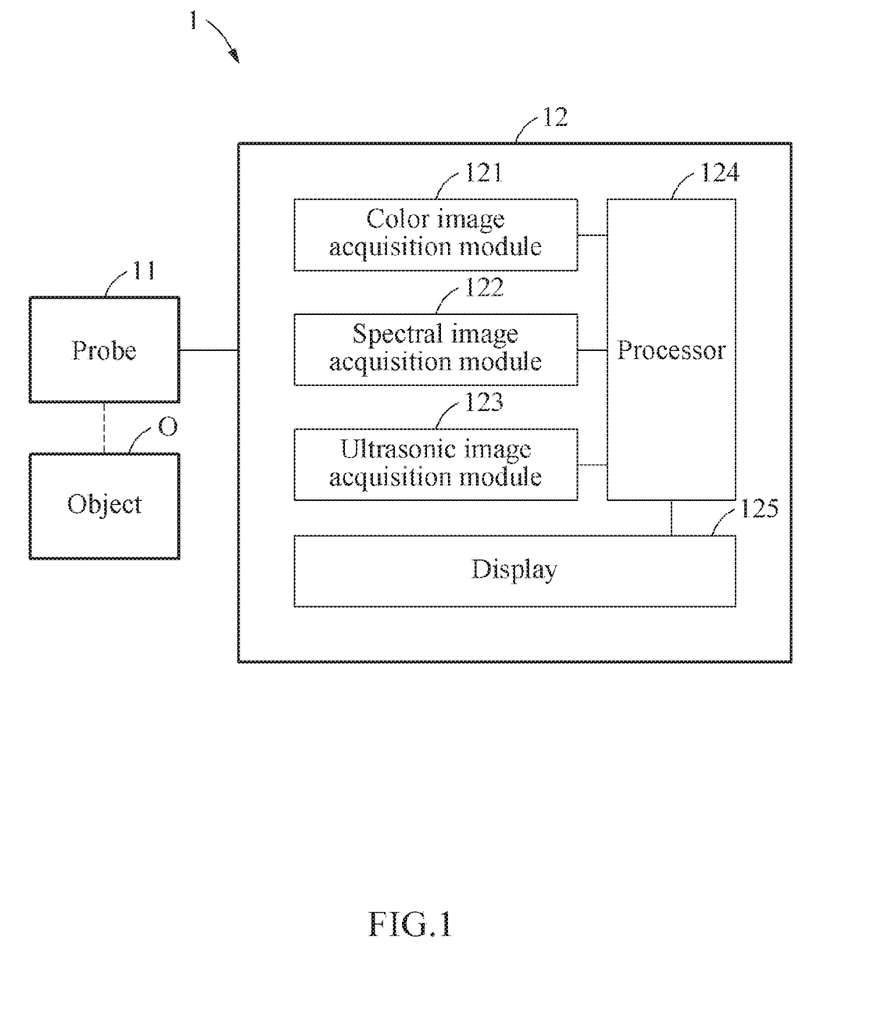
FIG. 1 is a block diagram illustrating a dental structure imaging system according to an example embodiment.

FIG. 1 is a block diagram illustrating a dental structure imaging system according to an example embodiment.

Referring to FIG. 1, a dental structure imaging system 1 may acquire an image of a dental structure of an object O, by obtaining surface information of the dental structure of the object O using an optical signal together with obtaining depth information of the dental structure of the object O using an ultrasonic signal. For example, the dental structure imaging system 1 may detect a position of a dental pulp, which is loose connective tissue, filling the anatomical space in a tooth, that is, a root canal and a pulp cavity. However, example embodiments are not necessarily limited thereto. The dental structure imaging system I may detect a position of a predetermined dental structure of the object O having surface information and depth information.

The dental structure imaging system 1 may include a probe 11 and an image processing system 12.

The probe 11 may be configured to be positioned in the dental structure of the object O. The probe 11 may receive the optical signal and the ultrasonic signal from the dental structure of the object O. In an example, the probe 11 may receive the signals from the dental structure of the object O in real time. This may help with positioning the probe 11 in a region suspected as a position of a dental pulp through a color image acquired in real time while a user manipulates the probe 11.

The image processing system 12 may acquire a plurality of images of different types based on the optical signal and the ultrasonic signal received by the probe 11, register the acquired plurality of images, and selectively display a registered image to the user. The image processing system 12 may include a color image acquisition module 121, a spectral image acquisition module 122, an ultrasonic image acquisition module 123, a processor 124, and a display 125.

The color image acquisition module 121 may acquire the color image of the dental to structure of the object O based on the optical signal received by the probe 11. The color image acquisition module 121 may include a camera to acquire the color image of the dental structure of the object O. For example, the camera may include an RGB camera, a high-sensitivity charge-coupled device (CCD) camera, and the like. The acquired color image of the dental structure of the object O may be displayed to the user through the display 125, such that the user may position the probe 11 in the region suspected as the dental pulp of the dental structure through the displayed color image.

The spectral image acquisition module 122 may acquire a spectral image of the dental structure of the object O based on the optical signal received by the probe 11. For example, the spectral image acquisition module 122 may include a camera to acquire the spectral image of the dental structure of the object O. For example, the camera may include an RGB camera, a high-sensitivity CCD camera, and the like. The spectral image acquisition module 122 may separate the received optical signal using a plurality of optical filters.

The spectral image acquisition module 122 may include a reflective spectral image acquisition module and a fluorescence spectral image acquisition module. The reflective spectral image acquisition module may analyze surface-reflected light based on the optical signal received by the probe 11 and define a surface color of the dental structure. The fluorescence spectral image acquisition module may analyze a spectrum of fluorescence based on the optical signal received by the probe 11 and measure an intensity of the fluorescence by changing the intensity into a photocurrent.

The ultrasonic image acquisition module 123 may acquire the ultrasonic image of the dental structure of the object O based on the ultrasonic signal received by the probe 11. For example, the ultrasonic image acquisition module 123 may include a pulser, a transmit-receive (TR) switch, a receiver, and the like, to acquire the ultrasonic image of the dental structure of to the object O.

The ultrasonic image acquisition module 123 may acquire the ultrasonic image of the dental structure using a high-frequency ultrasonic signal. If a high-frequency ultrasonic signal is used, substantially the same axial resolution as optical imaging equipment such as the spectral image acquisition module 122 may be achieved in a depth direction of the dental structure.

The processor 124 may be configured to register the spectral image acquired by the spectral image acquisition module 122 and the ultrasonic image acquired by the ultrasonic image acquisition module 123, to the color image acquired by the color image acquisition module 121. This may have an advantage in that a registered image has depth information and surface information of the dental structure in the same field of view and thus, may help the user with establishing an operation plan.

The display 125 may be configured to display an image registered by the processor 124. For example, the display 125 may include a cathode-ray tube (CRT) display, a liquid-crystal display (LCD), a plasma display panel (PDP), an organic light emitting diode (OLED) display, a field-emission display (FED), a light emitting diode (LED) display, a vacuum fluorescent display (VFD), a digital light processing (DLP) display, a primary flight display (PFD), a three-dimensional (3D) display, a transparent display, and the like, and include various other display devices within the scope obvious to one of ordinary skill in the art. Although not shown, the image processing system 12 may further include a communicator (not shown) configured to help with signal transmission and reception between subordinate elements thereof.

Meanwhile, the image processing system 12 may be provided integrally with the probe 1, but not limited thereto, and may be an external computer, a server, or the like. Further, the color image acquisition module 121, the spectral image acquisition module 122, the ultrasonic image acquisition module 123, the processor 124, and the display 125 may also integrally form a single unit. However, it may be understood that these elements may be implemented in various forms separately or in suitable combinations. For example, it may be implemented in the form of an electronic device including a portion of the subordinate elements of the image processing system 12.

Figure 2:
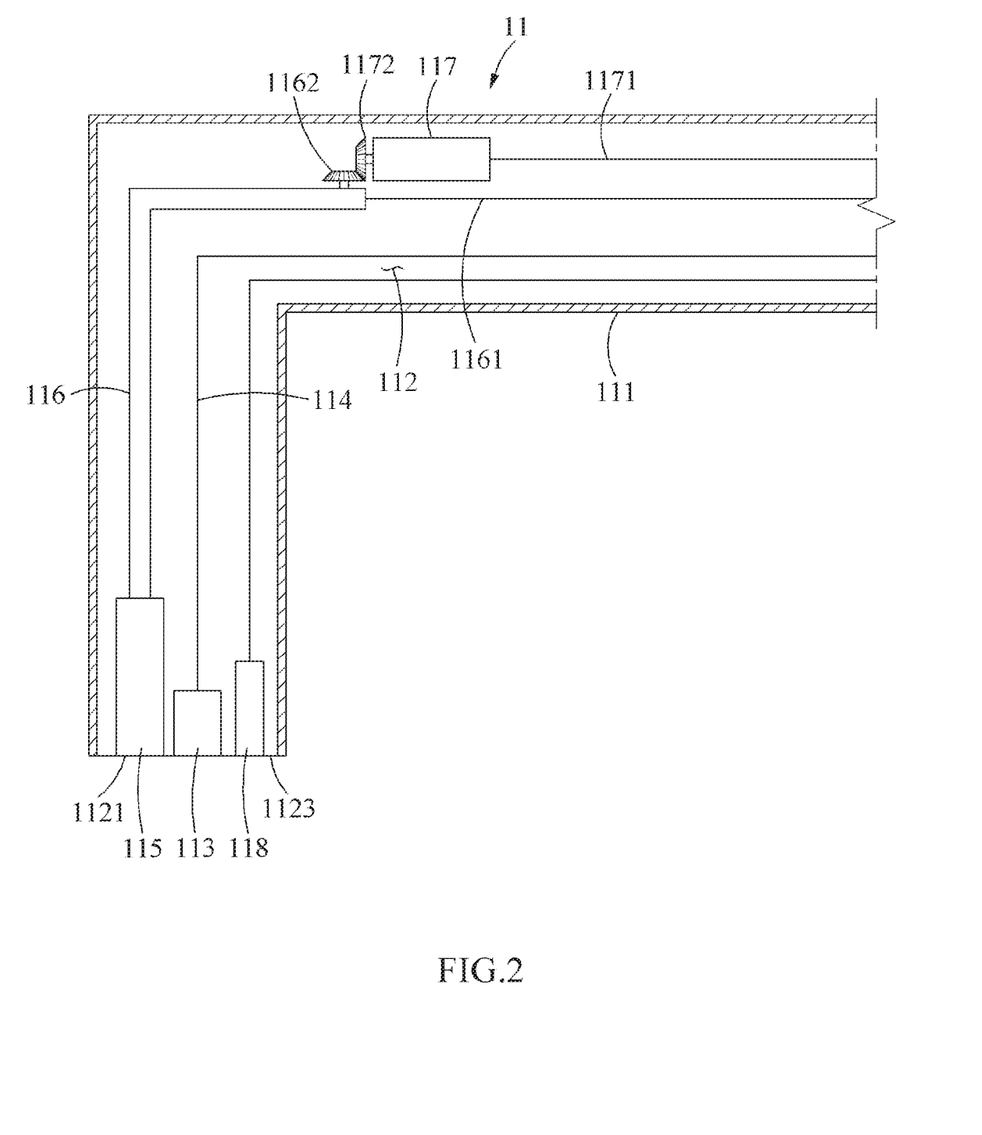
FIG. 2 is a cross-sectional view illustrating a probe according to an example embodiment.
Figure 3:
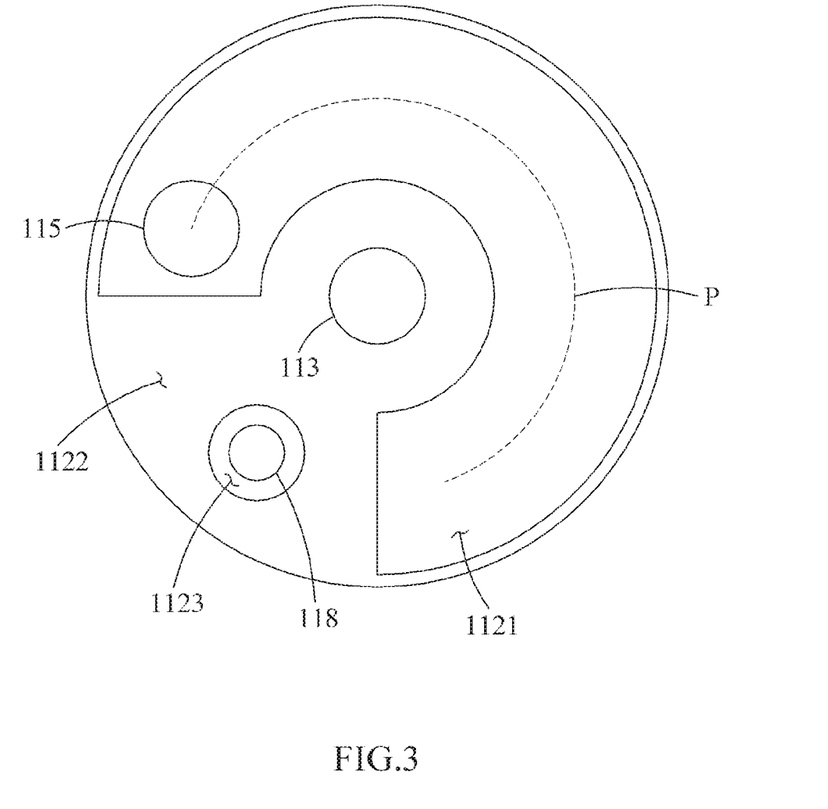
FIG. 3 is a view illustrating an end portion of a probe according to an example embodiment.

FIG. 2 is a cross-sectional view illustrating a probe according to an example embodiment, and FIG. 3 is a view illustrating an end portion of the probe according to an example embodiment.

Referring to FIGS. 2 and 3, the probe 11 may include a probe body 111, a working channel 112, at least one optical element 113, a bunch of optical fibers 114, an ultrasonic transducer 115, a drive shaft 116, and a driver 117.

The probe body 111 may have a predetermined shape suitable for accessing the dental structure of the object. For example, the probe body 111 may extend along a length direction and have a curved shape in which at least one curve is formed in the extending portion.

The working channel 112 may be provided in the probe body 111. The working channel 112 may be provided in the length direction of the probe body 111. The at least one optical element 113, the bunch of optical fibers 114, the ultrasonic transducer 115, the drive shaft 116, and the driver 117 may be arranged in the working channel 112.

The working channel 112 may include an arcuate slot 1121 formed in a circumferential direction based on the center of the working channel 112 at an end portion thereof, and a limiter 1122. In an example, the slot 1121 may have a length of about 270 degrees of the circumference based on the center of the end portion of the working channel 112, and the limiter 1122 may have a length of about 90 degrees of the circumference based on the center of the end portion of the working channel 112. In an example not shown, the slot 1121 may have a length of about 180 degrees of the circumference based on the center of the end portion of the working channel 112, and the limiter 1122 may have a length of about 180 degrees of the circumference based on the center of the end portion of the working channel 112. The slot 1121 and the limiter 1122 may also be referred to as a hole portion and a non-hole portion, respectively, in the structural aspect. The slot 1121 may extend from the front surface of the probe body 111 to the rear surface.

The working channel 112 may include a circular opening 1123 formed in the limiter 1122. A treatment device 118 configured to treat the dental structure, for example, the dental pulp, may be inserted into the circular opening 1123. The treatment device 118 may be connected to the processor 124 of the image processing system 12 or connected to a separate control device (not shown) and controlled through manipulation of the user or automatic control.

The at least one optical element 113 may be configured to transmit and receive optical signals to and from the dental structure of the object. For example, the at least one optical element 113 may include a lens. Preferably, the at least one optical element 113 may include an object lens. Further, the at least one optical element 113 may include a plurality of lens elements arranged in a row to guide the optical signal.

The bunch of optical fibers 114 may transmit an optical signal to the at least one optical element 113, or transmit an optical signal received from the at least one optical element 113 to the spectral image acquisition module 122. The bunch of optical fibers 114 may be connected to the at least one optical element 113, extend in the length direction of the working channel 112, and be connected to the spectral image acquisition module 122 (See FIG. 1).

The ultrasonic transducer 115 may be configured to transmit and receive ultrasonic signals to and from the dental structure of the object.

The at least one optical element 113 may be arranged at the center of the end portion of the working channel 112, and the ultrasonic transducer 115 may be arranged on an outer side of the at least one optical element 113. For example, the at least one optical element 113 may be provided at the center of the end portion of the working channel 112 in the form enclosed by the arcuate slot 1121, and the ultrasonic transducer 115 may move in the vicinity thereof along a path P of the slot 1121. The movement of the ultrasonic transducer 115 may be limited by the limiter 1122, and a moving distance thereof may be defined by the circumferential length of the limiter 1122. In an example, the ultrasonic transducer 115 may be configured to rotate about the at least one optical element 113.

The drive shaft 116 may be connected to the ultrasonic transducer 115, and configured to move the ultrasonic transducer 115. For example, the drive shaft 116 may rotate about the center of the working channel 112, such that the ultrasonic transducer 115 connected to the drive shaft 116 may rotate along the circumference of the working channel 112. The drive shaft 116 may include at least a portion of an electrical lead 1161 connecting the ultrasonic transducer 115 and the ultrasonic image acquisition module 123. Further, the drive shaft 116 may extend toward the end portion of the working channel 112 to be suitable for the shape of the working channel 112, and include a control device (not shown) configured to adjust a rotation of the ultrasonic transducer 115 and an angle with respect to an axial direction. Accordingly, a direction of a beam of the ultrasonic transducer 115 connected to the drive shaft 116 may be adjusted.

The driver 117 may be configured to generate power. The driver 117 may be mechanically connected to the drive shaft 116. For example, gears 1162 and 1172 may be provided at the end portion of the drive shaft 116 and the end portion of the driver 117, respectively, to engage with each other, and the power generated by the driver 117 may be transmitted to the drive shaft 116 by the engagement of the gears 1162 and 1172. The driver 117 may be driven by the image processing system 12 (See FIG. 1) or another controller, and be connected to the element through the electrical lead 1171.

Figure 4:
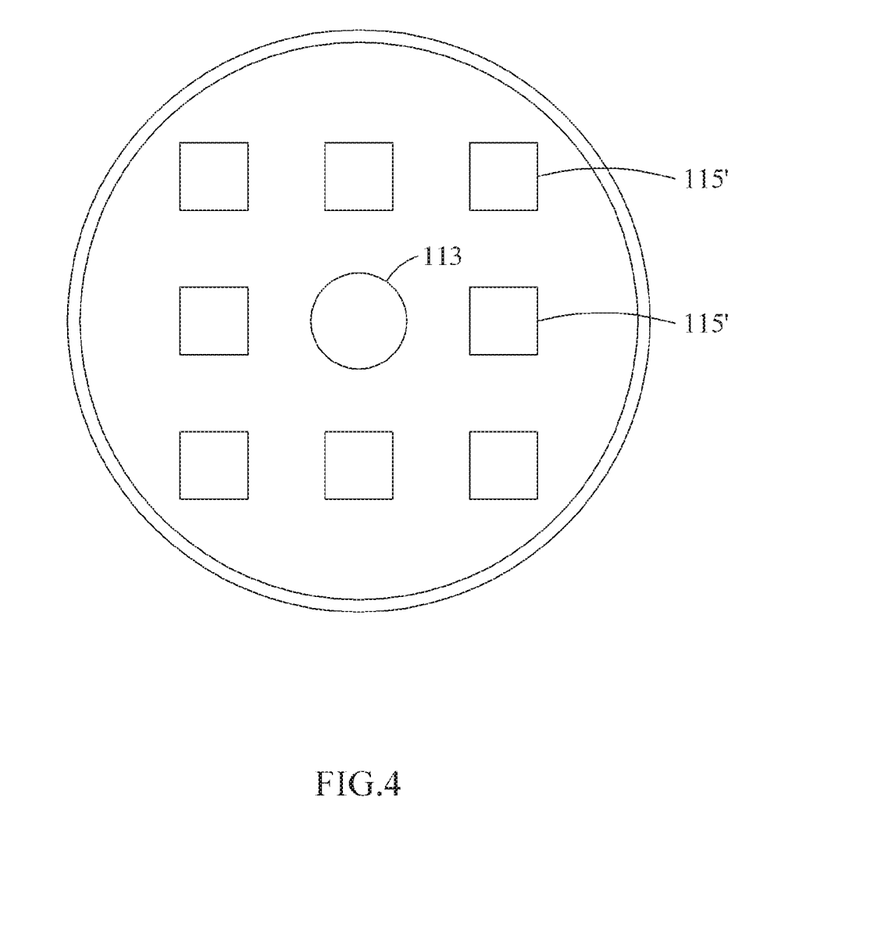
FIG. 4 is a view illustrating an end portion of a probe according to another example embodiment.

FIG. 4 is a view illustrating an end portion of a probe according to another example embodiment.

Referring to FIG. 4, a probe may have a structure in which an optical element 113 is arranged at the center of an end portion thereof, and a plurality of ultrasonic transducers 115' are arranged in the vicinity of the optical element 113. For example, the plurality of ultrasonic transducers 115' may be arranged in the form of a matrix at the end portion of a working channel. The number of ultrasonic transducers 115' is not limited. However, ultrasonic signals respectively received by the plurality of ultrasonic transducers 115' have depth information of divided regions of a dental structure, and thus the degree of precision of ultrasonic images may improve.

In an example not shown, the plurality of ultrasonic transducers 115' may be configured to rotate about the optical element 113. In this example, a circumferentially arcuate slot (not shown) through which the plurality of ultrasonic transducers 115' move may be provided at the end portion of the working channel.

Figure 5:
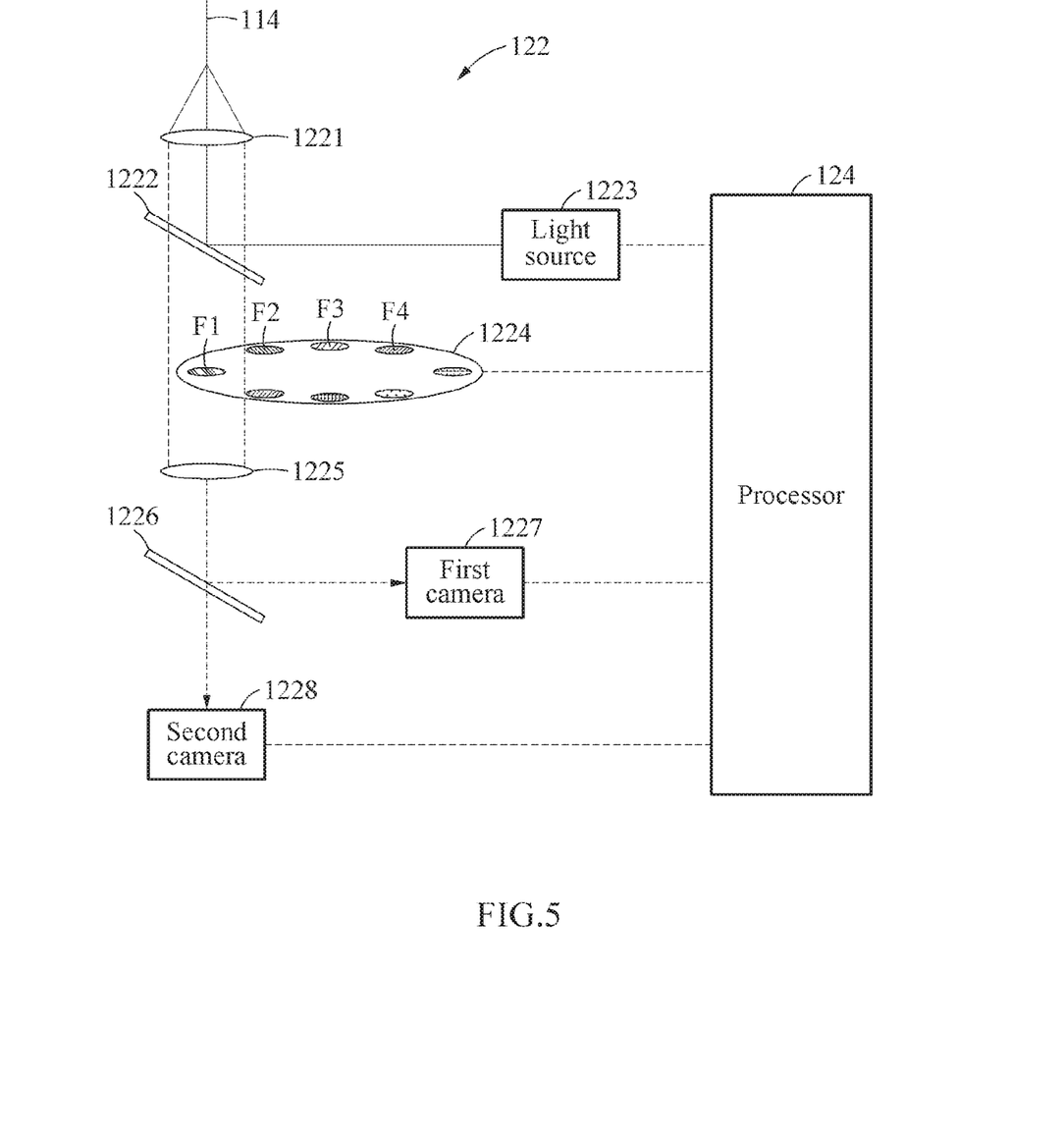
FIG. 5 is a view illustrating a spectral image acquisition module according to an example embodiment.

FIG. 5 is a view illustrating a spectral image acquisition module according to an example embodiment.

Referring to FIG. 5, the spectral image acquisition module 122 may be configured to transmit and receive optical signals through the bunch of optical fibers 114. For example, the spectral image acquisition module 122 may include a collimator 1221, a dichroic mirror 1222, a light source 1223, a filter wheel 1224 including a plurality of filters F1, F2, F3, and F4, a tube lens 1225, a beam splitter 1226, a first camera 1227, and a second camera 1228. The light source 1223 may include light sources of various wavelengths. For example, the light source 1223 may include a white light, a ultraviolet (UV) light source, and a plurality of short-wavelength light sources.

When the filter wheel 1224 is rotated, an optical path may be aligned with one (F1) of the plurality of filters F1, F2, F3, and F4, and the optical signal received through the bunch of optical fibers 114 may pass through the collimator 1221 and then pass through the filter F1 along the aligned optical path. Here, the plurality of filters F1, F2, F3, and F4 may include band-pass filters that pass optical signals of different bands. The optical signal of a set band passing through the filter F1 may be transmitted to the first camera 1227 and the second camera 1228 by the beam splitter 1226. Here, the first camera 1227 and the second camera 1228 may be an RGB camera and a high-sensitivity camera, respectively. Conversion to a color image and a spectral image may be performed by the respective cameras, and the color image and the spectral image may be transmitted to the processor 124 for image processing. The filter wheel 1224 may include a single empty space (not shown) where no optical filter is positioned for an RGB image, a fluorescent image, and the like.

Meanwhile, the light source 1223 may be controlled by the control of the processor 124. The light source 1223 may be configured to transmit an optical signal. The optical signal may be reflected by the dichroic mirror 1222 and incident to the collimator 1221. The optical signal incident to the collimator 1221 may be transmitted to the optical element 113 (See FIG. 2) through the bunch of optical fibers 114.

Figure 6:
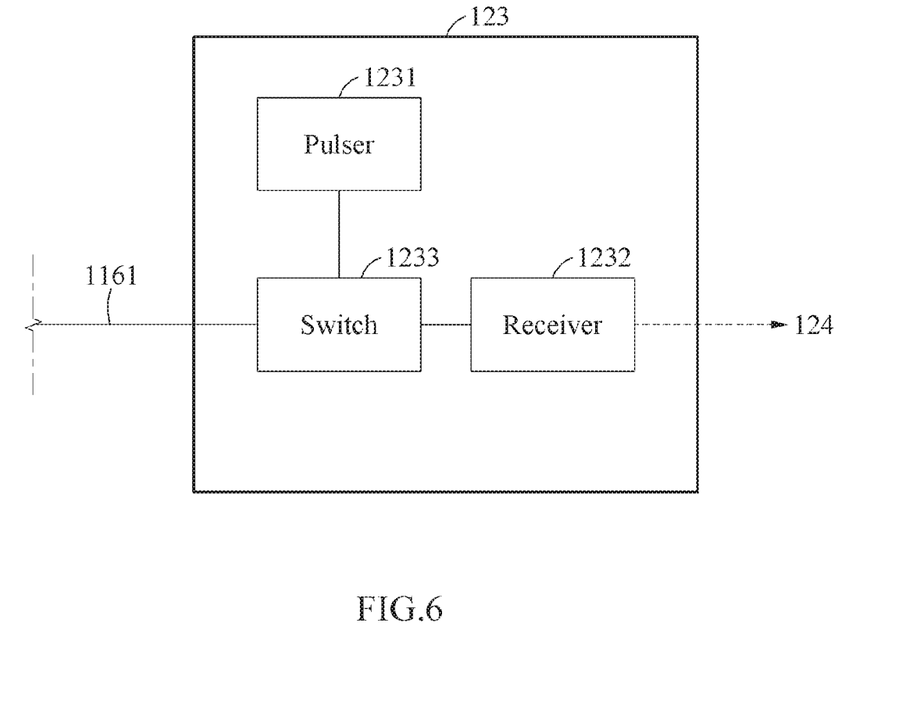
FIG. 6 is a view illustrating an ultrasonic image acquisition module according to an example embodiment.

FIG. 6 is a view illustrating an ultrasonic image acquisition module according to an example embodiment.

Referring to FIG. 6, the ultrasonic image acquisition module 123 may include a pulser 1231, a receiver 1232, and a switch 1233. The pulser 1231 may be configured to generate an electrical pulse according to ultrasonic vibration in the range of several MHz to hundreds of MHz. The receiver 1232 may be configured to receive the ultrasonic signal received through the electrical lead 1161. The receiver 1232 may generate an ultrasonic image based on the received ultrasonic signal. However, example embodiments are not limited thereto. For example, the receiver 1232 may transmit the received ultrasonic signal to the processor 124, and the processor 124 may generate an ultrasonic image based on the ultrasonic signal. The switch 1233 may be configured to selectively connect one of the pulser 1231 and the receiver 1232 to the electrical lead 1161. For example, the switch 1233 may include a TR switch.

Figure 7:
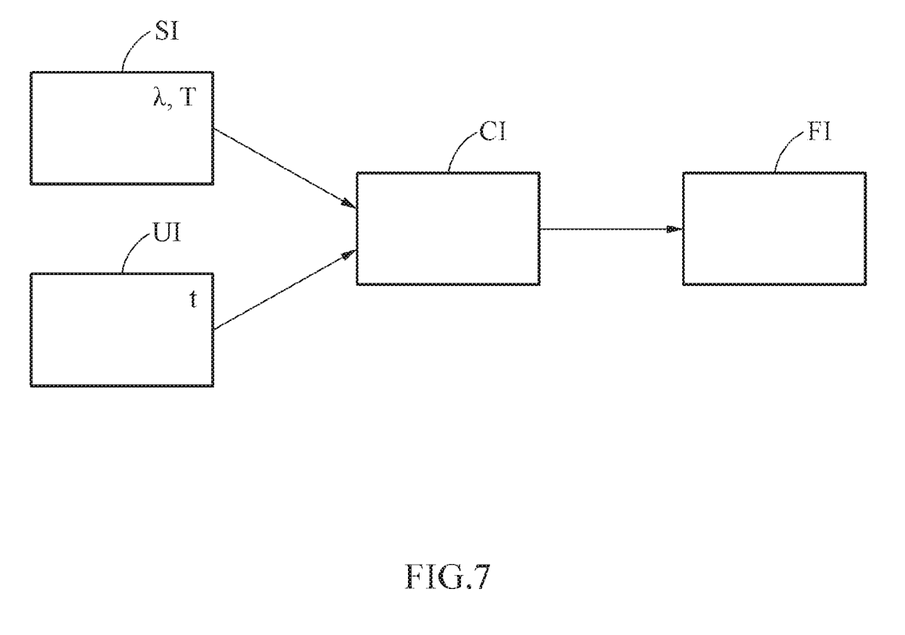
FIG. 7 is a view illustrating an image registration process of a dental structure imaging system according to an example embodiment.

FIG. 7 is a view illustrating an image registration process of a dental structure imaging system according to an example embodiment.

Referring to FIG. 7, a dental structure imaging system may register a spectral image SI represented by parameters such as a wavelength k and an intensity T and an ultrasonic image UI represented by parameters such as a depth t, to a color image CI having an RGB value. A registered image FI may have the RGB value being color information, the values of the wavelength $\lambda$ and the intensity T according to a spectral spectrum, and the value of the depth t on the same field of view.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

What is claimed is:

1. A probe, comprising:
   a working channel;
   at least one optical element provided within the working channel and configured to acquire a spectral image of surface information of an object; and
   an ultrasonic transducer arranged within the working channel and configured to acquire an ultrasonic image of depth information of the target and move with respect to the at least one optical element,
   wherein the ultrasonic transducer is configured to rotate about the at least one optical element.

2. The probe of claim 1, wherein the at least one optical element is positioned at the center of the working channel, and
   the ultrasonic transducer is positioned radially outward from the at least one optical element within the working channel.

3. The probe of claim 1, wherein the working channel further comprises an end wall having an arcuate slot extending around the at least one optical element along at least a portion in the vicinity of the at least one optical element, such that the ultrasonic transducer moves within the arcuate slot.

4. The probe of claim 3, wherein the working channel further comprises a limiter provided along a remaining portion in the vicinity of the at least one optical element and configured to limit a movement of the ultrasonic transducer.

5. The probe of claim 1, further comprising:
a driver configured to generate power; and
a drive shaft disposed within the working channel and configured to adjust a direction of a beam of the ultrasonic transducer by receiving the power from the driver and adjusting a rotation of the ultrasonic transducer and an angle with respect to an axial direction.

6. The probe of claim 5, wherein the working channel has a shape curved in a length direction thereof, and
the drive shaft extends along the curved shape.

7. A system for imaging a dental structure, comprising:
a probe configured to be positioned in a dental structure, the probe including:
 a working channel extending there through;
 an optical element disposed within the working channel; and
 an ultrasonic transducer disposed within the working channel and configured to transmit and receive an ultrasonic signal, the ultrasonic transducer configured to rotate about the optical element;
a spectral image acquisition module provided within the working channel and configured to acquire a spectral image of surface information of the dental structure;
an ultrasonic image acquisition module provided within the working channel and configured to acquire an ultrasonic image of depth information of the dental structure; and
a processor configured to register the spectral image and the ultrasonic image.

8. The system of claim 7, further comprising:
a color image acquisition module configured to acquire a color image of the dental structure,
wherein the processor is configured to register the spectral image and the ultrasonic image to the color image.

9. The system of claim 7, wherein the probe further comprises:
a lens configured to collect an optical signal from the dental structure; and
at least one optical fiber configured to transmit the optical signal collected by the lens,
wherein the spectral image acquisition module comprises a filter wheel including a plurality of filters configured to receive the optical signal by selecting a wavelength of the optical signal received from the optical fiber by rotating the filter wheel to align a corresponding one of the plurality of filters with the optical signal.

10. The system of claim 7, wherein
the ultrasonic image acquisition module comprises:
a pulser configured to adjust a pulse of the ultrasonic signal;
a receiver configured to receive the ultrasonic signal; and
a switch configured to open and close a signal transmission between the ultrasonic transducer and the receiver.

* * * * *